(12) United States Patent
Shih et al.

(10) Patent No.: US 8,945,480 B2
(45) Date of Patent: Feb. 3, 2015

(54) APPARATUS AND METHODOLOGY TO CARRY OUT BIOCHEMICAL TESTING ON A CENTRIFUGAL PLATFORM USING FLOW SPLITTING TECHNIQUE

(71) Applicant: Feng Chia University, Taichung (TW)

(72) Inventors: Chih-Hsin Shih, Taichung (TW); Ho-Chin Wu, Taichung (TW); Yu-Ping Yang, Taichung (TW)

(73) Assignee: Feng Chia University, Taichung (TW)

( * ) Notice: Subject to any disclaimer, the term of this patent is extended or adjusted under 35 U.S.C. 154(b) by 0 days.

(21) Appl. No.: 13/763,620

(22) Filed: Feb. 8, 2013

(65) Prior Publication Data
US 2014/0038209 A1 Feb. 6, 2014

(30) Foreign Application Priority Data
Aug. 1, 2012 (TW) .............................. 101127720 A (51) Int. Cl.
*B01L 3/00* (2006.01)
*G01N 33/53* (2006.01)

(52) U.S. Cl.
CPC ...... *G01N 33/5302* (2013.01); *B01L 3/502738* (2013.01); *B01L 3/502746* (2013.01); *B01L 2200/0605* (2013.01); *B01L 2300/0803* (2013.01); *B01L 2300/0864* (2013.01); *B01L 2300/0883* (2013.01); *B01L 2400/0409* (2013.01); *B01L 2400/0688* (2013.01); *B01L 2400/086* (2013.01)

USPC .............. 422/504; 422/417; 422/64; 435/7.1; 435/7.92; 435/287.3; 436/45

(58) Field of Classification Search
CPC ........ C12M 1/34; B01L 2200/10; B01L 3/00; B01F 13/00; A61K 47/48; G01N 21/03; G01N 21/07; G01N 1/18; F16K 99/0001
See application file for complete search history.

(56) References Cited

U.S. PATENT DOCUMENTS

| | | | |
|---|---|---|---|
| 2002/0106786 A1* | 8/2002 | Carvalho et al. | 435/287.3 |
| 2005/0196779 A1* | 9/2005 | Ho et al. | 435/6 |
| 2006/0194273 A1* | 8/2006 | Thomas | 435/29 |
| 2008/0102537 A1* | 5/2008 | Harding et al. | 436/514 |

* cited by examiner

*Primary Examiner* — Melanie Y Brown
*Assistant Examiner* — Rebecca Martinez
(74) *Attorney, Agent, or Firm* — Cheng-Ju Chiang (57) ABSTRACT

The invention provides an apparatus and methodology to carry out biochemical testing on a centrifugal platform using flow splitting technique. In conventional biochemical testing, reagents need to be loaded individually into each reservoir. By using the flow splitting technique in this invention, one reagent only need to be loaded once, then, it can be evenly distributed into each reaction chambers in single or multiple layers format. The invention greatly reduces the required manpower when large numbers of assays are integrated on one platform. Because of the invention, many medical examinations can be performed efficiently, thus reduce the waste of manpower, time and cost.

17 Claims, 6 Drawing Sheets

APPARATUS AND METHODOLOGY TO CARRY OUT BIOCHEMICAL TESTING ON A CENTRIFUGAL PLATFORM USING FLOW SPLITTING TECHNIQUE

BACKGROUND OF THE INVENTION

1. Field of the Invention

This present invention relates to a rapid test apparatus, more particularly to the rapid test apparatus in which the procedure comprising several times of injection of the same type reagent or injection of various types of reagents.

2. Description of Related Art

Take the sandwich ELISA for example. Capture antibody, antigen, detection antibody labeled with HRP, and chromogen solution are required to be loaded in sequence in this experiment. Because each step requires an incubation time and washing process, the overall sandwich ELISA often takes much time, even days, to accomplish the whole procedures. The conventional procedure using 96-wells microtiter plate must manually and repeatedly load the samples into the wells which not only wastes time but manpower.

In order to solve the problems stated above, Lee et al., in 2001, proposed microfluidic disc platform ELISA, abbreviated "CD-ELISA." According to the testing procedures, the system utilizes rotational speed to control the reagents sequentially being released; therefore, the technologist just simply loads the reagents into each reservoir in advance, then the system will automatically carry out the reagent releasing and mixing processes.

The principle of CD-ELISA illustrates as follows: scribe multiple microfluidic channels on a microfluidic disc to form a number of reservoirs, and place microfluidic valves beneath those reservoirs. When the microfluidic disc rotates at a low speed, the liquid from the reservoirs to the entrance of the microfluidic valves will form a liquid-gas interface, and the pressure inside the liquid is also formed by centrifugation; besides, a capillary pressure obstructing the liquid from proceeding is generated by the surface tension on the liquid-gas interface. When the rotational speed increases, so does the liquid pressure, as the pressure is greater than capillary pressure, the liquid will break through the microfluidic valves and subsequently flow out of the reservoirs. On the contrary, the liquid is retained in the reservoirs if its pressure is less than capillary pressure.

Such design not merely simplifies the procedures but diminishes the volume of reagents required and broadens the reaction surface area. These improvements may accelerate the entire process, so that the overall detection time is shortened to 1 to 2 hours to complete.

However, in the execution of CD_ELISA, there are still some problems that need to be overcome. Suppose five kinds of reagents are required to be loaded in the process, and in each procedure, five microfluidic valves are needed. It is learned from references that for the sake of breaking through the microfluidic valves, each (burst) rotational speed, from the outer part of the microfluidic disc to the inner part, has to reach 327, 546, 968, 1180 and 1506 revolutions per minute (RPM) individually; nevertheless, due to the shape of the disc, there is no way to speed up the (burst) rotational speed to enlarge the gap. It seems like the releasing of reagents in sequence could be controlled by different rotational speed, but in reality, each (burst) rotational speed is not a constant value, instead, the value falls in the average of (burst) rotational speed plus or minus 20% within the range. Therefore, the foregoing fact influences the correctness of releasing the reagents in sequence. If the gap of the (burst) rotational speed between each microfluidic valve is not big enough, the range of each speed may overlap resulting in bursting more than one microfluidic valves at the same time under the same rotational speed, and this situation will lead the test to fail.

In the year of 2009, Cho et al. proposed using laser irradiated ferrowax microvalve to replace microfluidic valve as the device for obstructing the liquid from releasing. Use low melting-point wax to block the microvalves so that the reagents cannot burst the ferrowax microvalves but stay in the reservoirs. As the liquid should be released, laser will be applied to melt the wax to open the microvalves and release the liquid in sequence. Though the method can properly control when to burst the valves to avoid releasing the liquid in wrong order, it becomes more difficult to make the disc, in addition, a sophisticated machine is needed to perform the task, hence the cost of entire tests increases.

Without considering the huge cost, even if the ferrowax microvalves has solved the problem of unstable (burst) rotational speed of the microfluidic valve, during the test, a large quantity of liquid to be injected are still required. Suppose there are 12 sets of microfluidic channels on a microfluidic disc and 5 reservoirs within each set of the microfluidic channels, the reagents require to be injected in for 60 times. Again, it takes lots of time and manpower along with the volatilization problem. Considering the manufacture of products in the future, the fixed cost of making microfluidic discs must be amortized in order to achieve economic benefits via placing more sets of microfluidic channels on one disc. If 96 sets of microfluidic channels are arranged on a microfluidic disc and 5 reservoirs in each set of microfluidic channels, with each set of microfluidic channel to be loaded for 5 times, there are total 480 times for the reagents to be injected in the whole detection system. Thus it is sure time and labor consuming, and the man-made negligence error would be likely to rise.

"Flow splitting channels" might be a solution to the problems stated above; driven by the centrifugal force, the reagents only need to be injected once, and they will be automatically and evenly allocate to each reaction chamber. According to references, the principle of the flow splitting mechanism can be divided into two types. One is the serial flow splitting, designed as a serial arrangement of splitting chambers, and each exit of the splitting chambers is controlled by valves. The principle is that the liquid driven by centrifugal force or capillary force splits in sequence to fill each splitting chamber, and which is obstructed by the valves, then the excess liquid would be discharged to the waste chamber through the end of the flow splitting channel, so that each splitting chamber would fill with same volume of liquid, eventually, for the purpose of evenly allocating the liquid, the rotational speed would be speeded up for the liquid to break through the valves to the reaction chambers. In the year of 2005 and 2009, Anderson and Mark et al. proposed the serial flow splitting. In this manner, however, the liquid fills in sequence, and therefore takes longer time to split; moreover, the capillary force is easily unstable while filling up the splitting chambers, prone to failure of splitting.

The other type is the crotched flow splitting, its structure shapes as follows, a crotched flow channel is divided into two channels, and these two channels are further divided into four channels. The principle is that the liquid driven by centrifugal force flows into the crotched flow channels and it further divides into several branches flowing into the reaction chambers. Lee et al. in 2009 proposed combining CD_ELISA and the crotched flow channels; however, while the liquid splits, such design may easily be affected by the Coriolis force produced from the rotation of the disc, which makes the flow opposite to the direction of the flow channel as the disc rotates larger and causes the allocation of the liquid uneven. Although Lin et al. in 2010 proposed the effect of the Coriolis force could be reduced by amending the geometric shapes of the crotched flow channels to lower the rotational speed, the test result had demonstrated that in order to achieve the expected objective, the rotational speed should not exceed 1000 RPM. Once more, the problem has remained unsolved.

SUMMARY OF THE INVENTION

The present invention proposes an apparatus using flow splitting technique to carry out biochemical tests, also called disc flow splitting test system for solving the problems stated in the related prior arts. The present invention provides a function of controlling the flow splitting via the design of structures symmetrical to the center to prevent the interference from the Coriolis force in θ direction. On the contrary, with the present invention, the Coriolis force may help the liquid to split into a splitting chamber. Furthermore, the design of the present invention is parallel splitting and utilizes centrifugal force instead of capillary force to drive the liquid, which can hasten the liquid to be split into the splitting chambers simultaneously and reduce irregular flow. Consequently, the present invention not only possesses the advantages of the conventional CD_ELISA but greatly decreases the reagent injection times. The liquid in the present invention can be reagents used in the tests, sample, washing liquid, or the combination thereof.

The present invention proposes an apparatus using flow splitting technique to carry out biochemical tests comprises a rotator platform and a microfluidic disc set on the rotator platform, both shaped like a disc, round and flat. wherein at least one notch set evenly on the periphery of the rotator platform, the microfluidic disc fixed on the rotator platform via the at least one notch, and to avoid influencing the results of the tests by materials, the material of the rotator platform can be a choice of aluminum, and the material of the microfluidic disc can be a choice of polymethylmethacrylate (PMMA).

The microfluidic disc comprises a layer of microfluidic structures, from the center to the periphery of the layer of the microfluidic structures comprising an injection chamber with a reagent injection orifice, set at the center of the layer of the microfluidic structures; at least one microfluidic channel arranged radially in the layer of the microfluidic structures and connected with the injection chamber, the at least one microfluidic channel used as the channel for liquid to flow through and for the reagents flowing from the center of the layer of the microfluidic structures to the periphery; at least one detection chamber with a sample injection orifice, placed at the periphery of the layer of the microfluidic structures and connected with the at least one microfluidic channel for the reagents to carry out reactions, and at least one waste chamber, placed next to and connected to the at least one detection chamber for waste storage after the reactions.

The at least one microfluidic channel comprises a splitting chamber set outside and connected with the injection chamber, equally splitting the reagents from the injection chamber, and a flow-resistant element placed between and connected with the splitting chamber and the at least one detection chamber, controlling the reagents flowing from the splitting chamber to the at least one detection chamber.

The layer of the microfluidic structures further comprises at least one mixing chamber with a sample injection orifice set between and connected with the flow-resistant element and the at least one detection chamber.

The layer of the microfluidic structures further comprises at least one secondary microvalve set between and connected with the at least one detection chamber and the at least one waste chamber, controlling the reagents flowing from the at least one detection chamber to the at least one waste chamber.

Volume of the splitting chamber is at least three times as much as the at least one detection chamber, and distance from each flow-resistant element of each at least one microfluidic channel to the center of the layer of the microfluidic structures is the same. The flow-resistant element has choices of a herringbone shape microvalve and a high-resistance-buffer flow channel.

To preclude the problem of microvalves being broken through at the same time caused by the former designs mentioned in the related prior arts, the present invention utilizes the splitting chamber in coordination with variant rotational speed to produce an inertial force of θ direction making the liquid split to each splitting chamber and a centrifugal force of r direction making the surface of the liquid stable and smooth. Meanwhile, if the flow-resistant element works as the microvalve, it can block the liquid. Because the distance from each microvalve to the center of the layer of the microfluidic structures is the same, the burst rotational speed of each microvalve is equal. Hence, it simply needs low rotational speed to split the reagents to each splitting chamber, then uses high rotational speed so that the reagents may burst the microvalve and flow to the detection chamber. At high rotational speed, the liquid on the surface of each microvalve could be removed so as to restore the obstructing function. Afterwards, other reagents can be loaded when necessary, and then repeat the step of bursting the microvalve. The advantages of the present invention are loading one reagent at a time to avoid the incorrectness of the releasing sequence, reducing the times of injection and easier to control the rotational speed.

For the sake of achieving economic benefits, a plurality of microfluidic channels are usually laid on one microfluidic disc. Suppose there are 96 microfluidic channels laid on one microfluidic disc and 5 reservoirs in each channel, it then requires 480 times for the reagents to be injected in this test. The apparatus carrying out biochemical tests using flow splitting technique utilizes the operation of splitting chamber to make each injected reagent equally split to each microfluidic channel. Thus, 5 kinds of the reagents require only 5 times injections to equally split to the 96 microfluidic channels. Compare to prior arts, the present invention obviously has the vantage in time and manpower saving.

In the procedure, liquid A flowing from the splitting chamber to the detection chamber will be replaced by liquid B coming from the splitting chamber after. The stability of signal detection of the reactions could be enhanced if liquid A fully replaces liquid B; therefore, the volume of the splitting chamber and the detection chamber plays an important role. To get a better effect of replacement, the volume of the splitting chamber must be at least three times as much as the detection chamber; moreover, based on different designs, the volume ratio of the two chambers could be six or even ten times.

If the flow-resistant element works as the microvalve, the change of geometric shape or increase of the hydrophobicity on the surface help to obstruct the liquid proceeding with low rotational speed. The designed shape of the microvalve comprises a round shape or a fish-bone shape. If the reagents comprise protein, the protein could stick to the wall of the microvalve with the round shape causing dysfunction. When the reagents flow the fish-bone shape microvalve, the reagents could easily remain in the microvalve causing the contamination between the reagents. Therefore, in the present invention, the angle of the fish-bone shape microvalve has been adjusted slightly, becoming the herringbone shape. The adjustment not only keeps the feature of the microvalve obstructing the liquid but avoiding the liquid remaining in the microvalve. This resolves the problem of the contamination between the reagents.

Some kinds of the liquid, for instance, Phosphate Buffer Solution with Tween-20 (PBST) could cause the permanent failure in the hydrophobicity of the microvalve after the liquid flow through the microvalve. The hydrophobicity cannot be regained with high rotational speed by removing the liquid on the surface of the microvalve. Hence, the high-resistance element could be adopted as the high-resistance-buffer flow channel. The geometric shapes, for instance, depth and width of the high-resistance-buffer flow channel are usually smaller than the injection chamber's or the at least one microfluidic channel's. With the different flow-resistance between the liquid in the high-resistance-buffer flow channel and in the injection chamber, the splitting chamber can be filled up with the liquid before the reagents flow through the high-resistance-buffer flow channel. Then raised the rotational speed again, the purpose of equally splitting the flow can be achieved.

The aforementioned disclosure has demonstrated the single side and single layer of the flow splitting technique. However, the design of the present invention does not confine to the single side and single layer and could be double sides and multiple layers depending on the need. The microfluidic disc could comprise at least two layers of the microfluidic structures. The at least two layers of the microfluidic structures, from the center to the periphery, comprise the injection chamber, the at least one microfluidic channel, the at least one detection chamber, the at least one waste chamber. The at least one microfluidic channel also comprises the splitting chamber and the flow-resistant element. In addition, the at least two layers of the microfluidic structures further comprise the at least one mixing chamber and the at least one secondary microvalve which located same as the single side and single layer.

The designed characteristic of the multiple layers is that the at least one detection chamber is connected with each at least one microfluidic channel which is in the different layers and placed at the same position corresponding to that in an upper layer and a lower layer of the at least two layers of microfluidic structures. If there are four layers of the microfluidic structures, in each layer, there are plural microfluidic channels. The at least one detection chamber is linked by the four microfluidic channels which are in the four different layers and which are corresponding to each other in each layer. The liquid in four microfluidic channels in the corresponding position in different layers flow into the same at least one detection chamber. Moreover, each injection chamber in different layers of the at least two layers of the microfluidic structures is not mutually connected and the injection chamber in each layer is with the reagent injection orifice. The distance between each flow-resistant element of each at least one microfluidic channel in the same layer of the at least two layers of microfluidic structures and the center of the at least two layers of microfluidic structures is the same. The distance in the same layer can be different with the distance in another layer.

The present invention does not confine to the double sides and double layers. If there are many kinds of reagents in the experiment, there could be double sides with three layers, four layers and even more. If the microvalve works as the flow-resistant element, comparing to the single side and single layer, the design of multiple layers can avoid the different reagents flowing through the same microvalve due to the injection into the different injection chambers in different layers. The problem of the dysfunctional microvalve which cannot obstruct the liquid due to the reagents comprising protein or surfactants flowing through the microvalve can be avoided. The contamination between the reagents can also be avoided. If the multiple layers are not adopted, after the microvalve is broken through, then we need the rotation of the rotator platform with a high rotational speed persists for certain time, for instance, 10 minutes, to dry up the microvalve, so the characteristic of obstructing the liquid can be regained.

DETAILED DESCRIPTION OF THE INVENTION

The present convention is in accordance with embodiments, trying to solve the disadvantages of prior arts.

Figure 1:
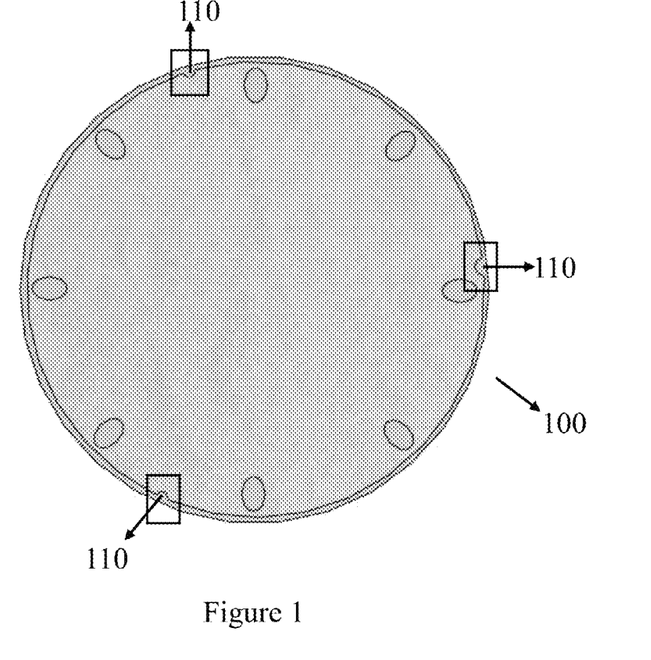
FIG. 1 illustrates a top view of the rotator platform.

FIG. 1 is one of the embodiments to demonstrate a rotator platform 100. The rotator platform 100 comprises at least one device on the rotator platform corresponding to at least one notch 110. By the at least one notch 110, a microfluidic disc 200 is fixed on the rotator platform 100.

Figure 2:
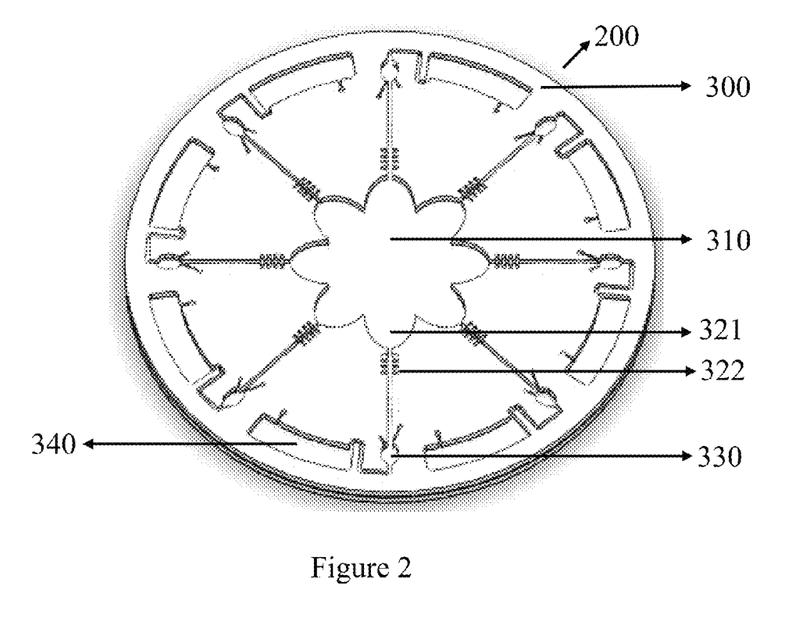
FIG. 2 illustrates the layer of the microfluidic structures.

In the FIG. 2, the microfluidic disc 200 comprises a layer of microfluidic structures 300. From the center to the periphery of the layer of the microfluidic structures 300 comprising: an injection chamber 310, a splitting chamber 321, a flow-resistant element 322, at least one detection chamber 330, and at least one waste chamber 340.

Figure 3:
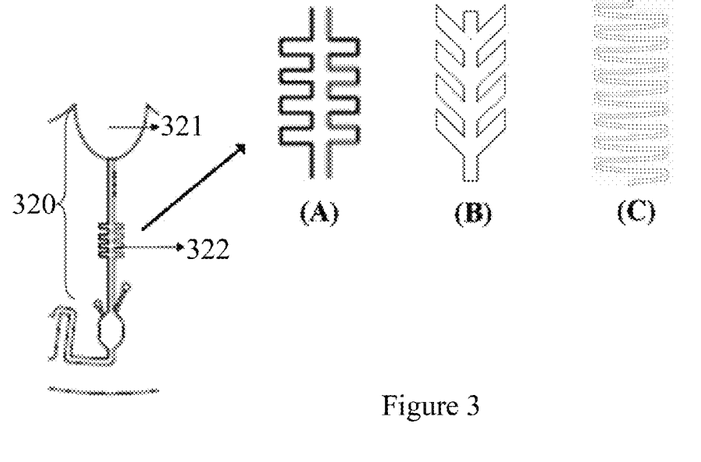
FIG. 3A illustrates the fish-bone shape microvalve.
FIG. 3B illustrates the herringbone shape microvalve.
FIG. 3C illustrates the high-resistance-buffer flow channel.

At least one microfluidic channel 320 comprises the splitting chamber 321 and the flow-resistant element 322. The flow-resistant element 322 has choices of microvalve with round shape or fish-bone shape the as shown in FIG. 3A. If reagents comprise protein, the protein could stick to the wall of the microvalve with the round shape causing dysfunction. The reagents could easily remain in the microvalve with the fish-bone shape causing contamination between the retain reagents and the current reagents. Accordingly, the present invention adopts the microvalve with the herringbone shape as shown in FIG. 3B, for keeping the function of obstructing the liquid or remains of the reagents. Some kinds of liquid, for instance, Phosphate Buffer Solution with Tween-20 (PBST) cause the permanent failure in the hydrophobicity of the microvalve after the liquid flows through the microvalve. The high-resistance-buffer flow channel could be adopted as the high-resistance element, as shown in FIG. 3C.

Figure 4:
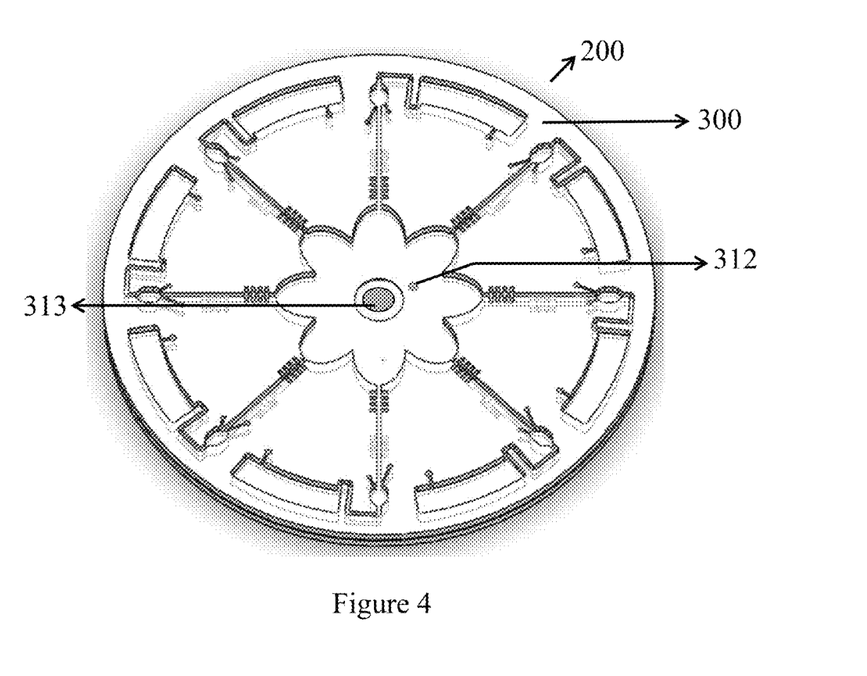
FIG. 4 illustrates a top view of the double sides and double layers of microfluidic structures.
Figure 5:
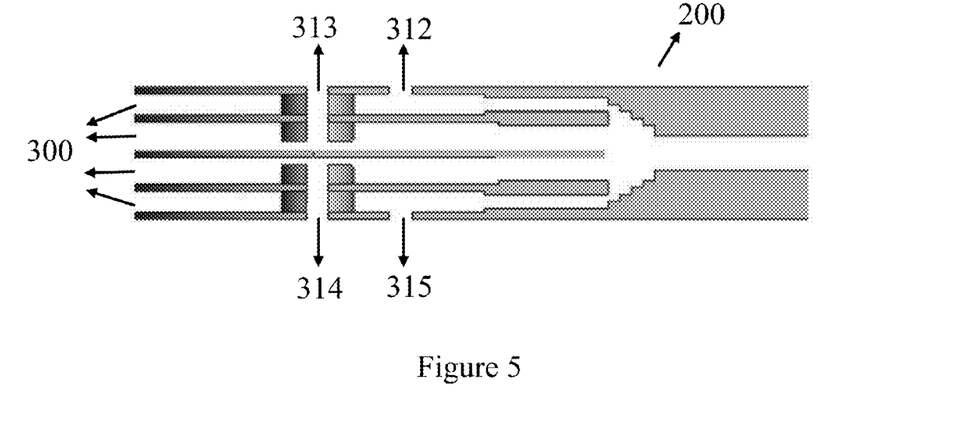
FIG. 5 illustrates a lateral sectional view of the double sides and double layers of microfluidic structures.

The present invention can provide multiple sides and multiple layers of microfluidic structures. FIG. 4 illustrates a top view of the double sides and double layers microfluidic structures 300. In the FIG. 5, it is a lateral sectional view of the double sides and double layers microfluidic structures 300. We can learn from the FIG. 5 that the microfluidic disc 200 comprises four layers of microfluidic structures 300. An individual injection orifice for the reagents is settled in each layer. The injection orifices of the multiple layer structures have shown in FIG. 5, for instance, the orifice of the first layer 312, the orifice of the second layer 313, the orifice of the third layer 314 and the orifice of the fourth layer 315. However, exits for the reagents of each layer join to one common chamber, the detection chamber 330.

Figure 6:
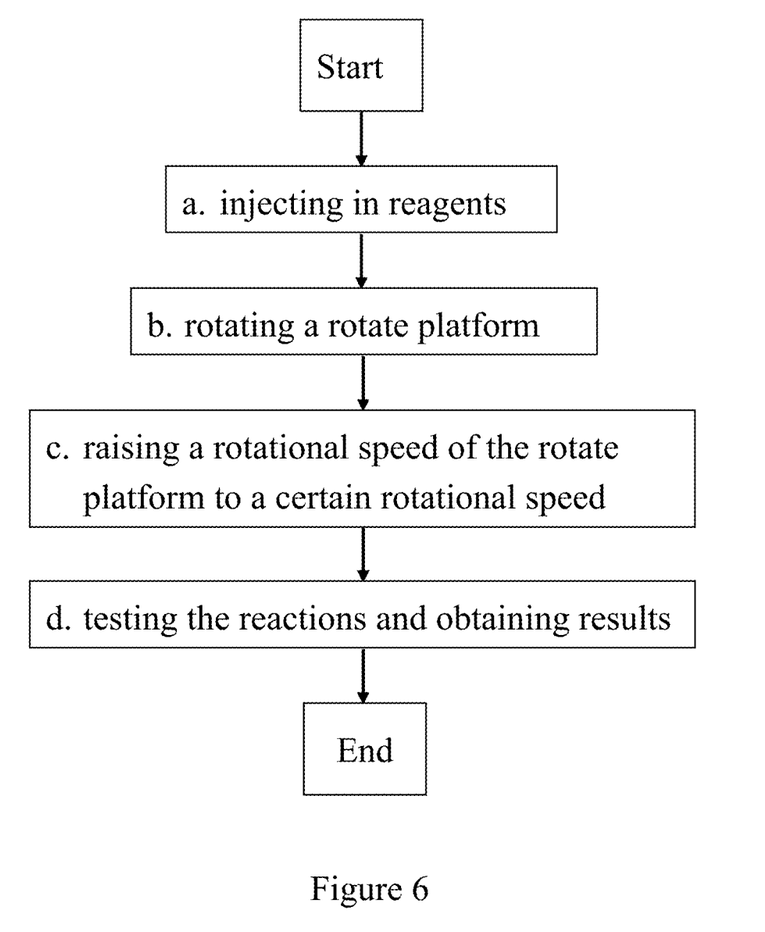
FIG. 6 illustrates a flowchart of the apparatus using flow splitting technique to carry out biochemical tests.

The FIG. 6, illustrates a flowchart of the apparatus using flow splitting technique to carry out biochemical tests, comprising the following steps: a. injecting the reagents: injecting the reagents into the injection chamber 310 or the at least one detection chamber 330; b. rotating the rotator platform 100: if the microvalve is the flow-resistant element 322, and rotating with a rotational speed under a burst rotational speed of the microvalve, making the reagents in the injection chamber 310 split equally into the splitting chamber 321 of the at least one microfluidic channel 320; c. raising the rotational speed of the rotator platform 100 to the certain rotational speed: after increasing to the certain rotational speed, the reagents in the splitting chamber 321 breaking through the microvalve and flow into the at least one detection chamber 330, mixing the reagents in the at least one detection chamber 330 to carry out the reactions; d. testing the reactions and obtaining results. In the step c, the certain rotational speed is a constant value. The constant value is decided by the position of the microvalve, the contact angle on the surface, and the geometric shape. When the step c is completed, the step b and c can be repeated depending on the need of the procedure and proceeding step d.

If the single layer is adopted, the method comprising the following steps: proceeding the step a, the reagent X is injected into the injection chamber 310 or the at least one detection chamber 330. Proceeding the step b, turning on the motor, after the motor rotates, the rotator platform 100 and the microfluidic disc 200 rotate with it. The reagent X is split equally into each splitting chamber 321. Because the rotational speed is not enough to break through the microvalve, the reagent X is obstructed in the splitting chamber 321. After the surface of the reagent X becomes smooth, the step c proceeding the high rotational speed makes the reagents break through the microvalve and makes the reagents flow into the at least one detection chamber 330. Keeping the high rotational speed for ten minutes makes the microvalve dry and regaining the characteristic of the microvalve to obstructing the proceeding of the reagents. If the need is necessary, injecting the reagent Y. Repeating the steps above, and finally proceeding the step d, the reactions are tested and the results are obtained.

If the multiple layers are adopted, the difference lies in step a, injecting the reagents. Different reagents can be injected in the injection chamber 310 in different layers. The reagent X is injected in the injection chamber 310 in the first layer of the microfluidic structures 300. Proceeding the step b, rotating the rotator platform 100. Proceeding the step c, raising the rotational speed of the rotator platform 100 to the certain rotational speed. The flow splitting technique makes the reagent X flow equally to the at least one detection chamber 330. Proceeding the step a again, the reagent Y is injected into the injection chamber 310 of the secondary layer of the microfluidic structures 300. Proceeding the step b again, rotating the rotator platform 100. Proceeding the step c, raising the rotational speed of the rotator platform 100 to the certain rotational speed. The flow splitting technique makes the reagent Y flow equally to the at least one detection chamber 330. The reagent Z is injected into the injection chamber 310 of the third layer of the microfluidic structures 300, as the step a, the rotator platform 100 rotates, as the step b, the rotational speed of the rotator platform 100 is raised to the certain rotational speed. As the step c, the flow splitting technique makes the reagent Y flow equally to the at least one detection chamber 330. At last, proceeding the step d, the reactions are tested and the results are obtained.

If the multiple layers are adopted, within the procedure, the different reagents are injected into the different injection chambers 310 in different layers. Then the reagents flow through the different splitting chambers 321 and the different flow-resistant elements 322. At last, the reagents flow into the common at least one detection chamber 330 for testing the reactions. The procedures can avoid the contamination between the reagents completely. If the microvalve is adopted as the flow-resistant element 322, the step of keeping the high rotational speed for certain time to dry up the microvalve can be omitted when the single layer of the microfluidic structures with multiple reagents are used.

One Preferable Embodiment

Figure 7:
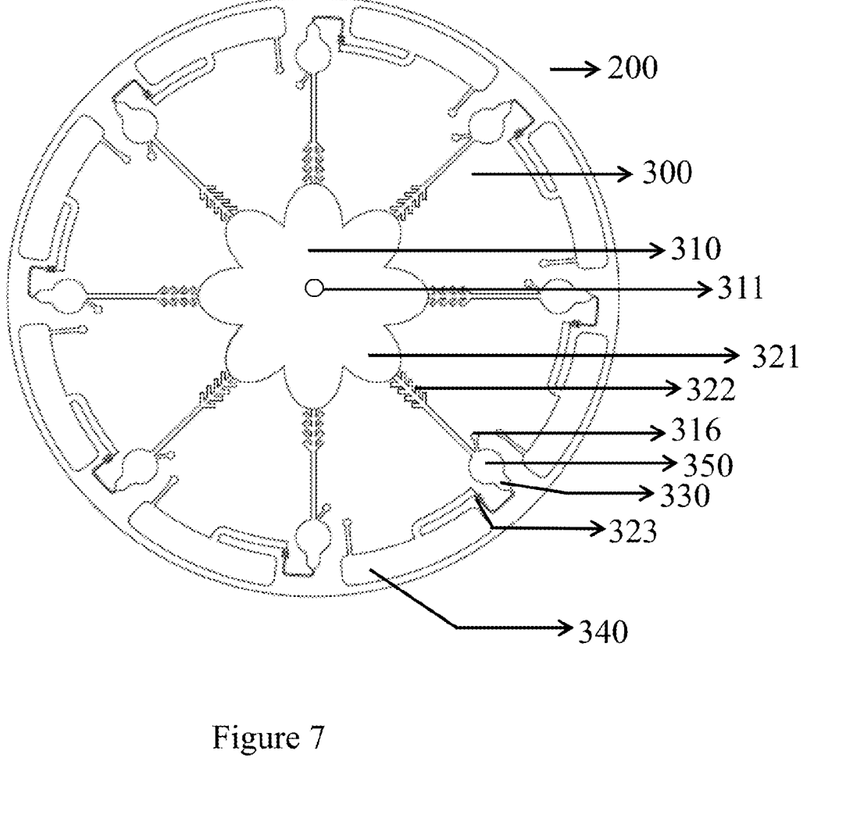
FIG. 7 illustrates the layer of the microfluidic structures for proceeding ELISA in one embodiment.

The preferable embodiment is single side and single layer of the microfluidic structures 300 and the microvalve is the flow-resistant element 322 for CD_ELISA. The microfluidic disc 200 of the preferable embodiment has shown in FIG. 7. First, 1 microliter (1 μL) of magnetic beads coated with capture antibody, 50 μL of antigen and 1 μL of detector antibody labeled with enzyme are injected into an injection orifice for the sample 316. Liquid of mixture of the reagents and sample flow to the at least one mixing chamber 350. Next, the microfluidic disc 200 is settled and fixed on the rotator platform 100. The motor rotates with 800 RPM. With at least one secondary microvalve 323, the liquid are obstructed in the at least one mixing chamber 350 and the liquid level of the liquid remains higher. Further, the magnetic beads are rolling due to the magnetic field for complete mixing. One-hour incubation is carrying out for basic bonding. After mixing, let the motor rotate at 1500 RPM and makes the liquid break through the at least one secondary microvalve 323. Meanwhile, the magnetic beads on which the capture antibody and antigen have been bonded fix in the at least one detection chamber 330 because of the magnetic field or the geometric shapes. The excess liquid is expelled to the at least one waste chamber 340. Then the 560 μL of washing liquid, for instance, Phosphate Buffer Saline with Tween-20(PBST) is injected into an orifice of the single layer 311. The rotational speed of the motor is 1000 RPM in accordance with the microvalve to let the PBST split full fill the splitting chamber 321. The rotational speed of the motor is raised to 4000 RPM making the washing liquid break through the microvalve and flow to the at least one detection chamber 330 and 70 μL of the washing liquid is split into the at least one detection chamber 330 washing for 2 minutes. At the same time, after the rotational speed of 4000 RPM for 10 minutes, the microvalve is dry and regains its characteristic. The washing step can be repeated depends on the need. Finally, 560 μL of the chromogen solution (TMB) is injected into the orifice of the single layer 311 and 70 μL of the chromogen solution is split into the at least one detection chamber 330. Under the magnetic field, the reactions are carrying out for 20 minutes. At last the reactions can be tested and the results can be obtained.

Another Preferable Embodiment

This preferable embodiment is single side and single layer of the microfluidic structures 300. The microvalve is the flow-resistance element 322. A Lipid test accounts for the procedures with the present invention. The microfluidic disc 200 of this preferable embodiment has shown in FIG. 8. The application of the present invention in the tests can reduce the time for physical examination. The results of the examination can be obtained faster.

Figure 8:
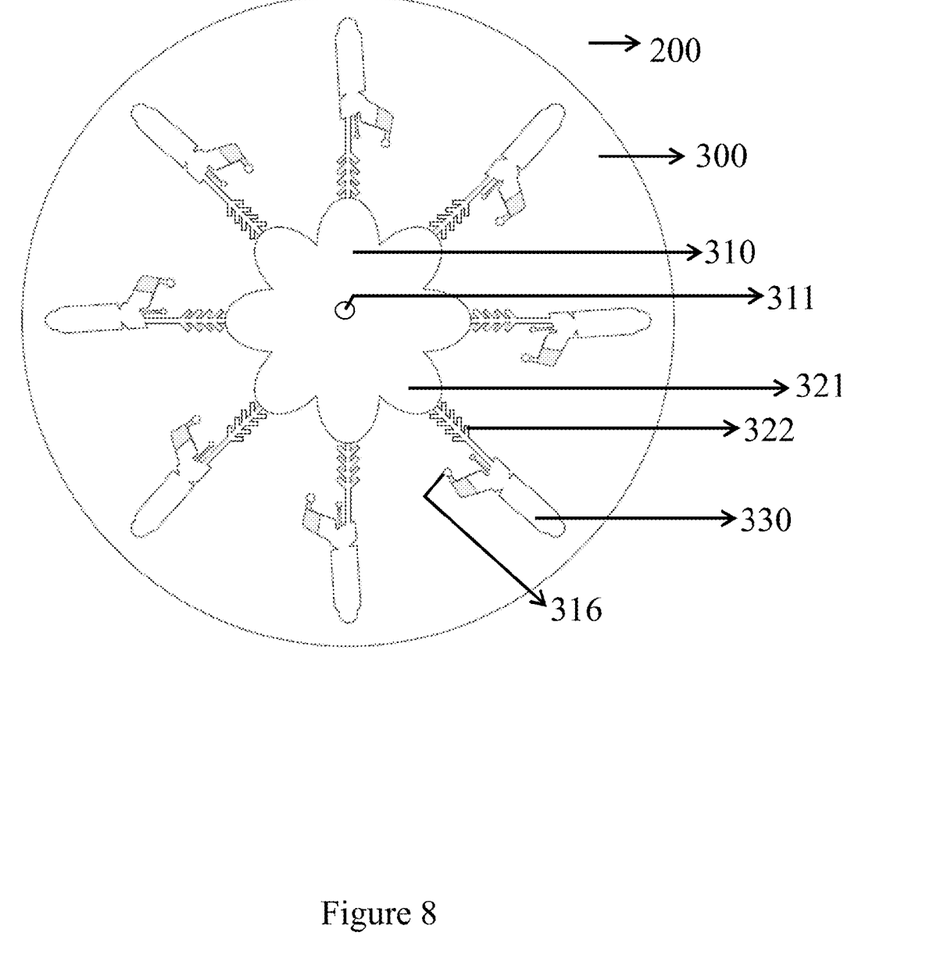
FIG. 8 illustrates the layer of the microfluidic structures for proceeding Lipid test with the present invention.

The Lipid test utilizes Enzymatic End Point Method to test the Triglycerides, TG, content in serum. First, 1 µL serum is injected into the injection orifice for the sample 316 and then flow to the at least one detection chamber 330. 272 µL reagent for the test is injected into the orifice of the single layer 311. The rotational speed of the motor is 1000 RPM in accordance with the microvalve to let the reagent for the test full fill the splitting chamber 321. The rotational speed of the motor is 4000 RPM making the reagent for the test break through the microvalve to the at least one detection chamber 330. 34 µL of the reagent for the test is split into the at least one detection chamber 330. The motor is set to rotate clockwise and counterclockwise for shaking and mixing; the amplitude is 150 degree, the frequency is 15 Hz, and the time is 30 seconds. After liquid of mixture of serum and the reagent for the test is mixed completely in the at least one detection chamber 330, the reaction can be tested.

The present invention providing an apparatus and methodology with flow splitting technique can be applied to carry out biochemical tests, especially to tests which require multiple reagents, for instance, immunological tests. In the ELISA, the capture antibody, antigen, detector antibody, washing liquid, chromogen solution are loaded or injected in sequentially. If there are 8 microfluidic channels 320 in the microfluidic disc 200, all the reagents required to be injected in for 40 times. With the design of the present invention, the reagents are only injected in for 5 times. Each reagent can be equally split into the at least one detection chamber 330 via the flow splitting technique. The purpose of carrying out ELISA is achieved.

By the aforementioned disclosure, the total times for injecting reagents can be reduced. Because only one reagent requires to be injected in one time and the equal distance between each flow-resistant element 322 to the center of the layer of the microfluidic structures 300, the technologist controls the high rotational speed of the microfluidic disc 200 for the reagents to release. There is no need to switch different rotational speeds. There is no need to consider the unstable burst rotational speed of each microvalve. The contamination between the reagents is without possibility. Therefore, the present invention can greatly simplify the procedure, raise convenience of operating and diminish the possibility of human errors. The present invention is definitely a good choice for biomedical examinations.

What is claimed is:

1. An apparatus using flow splitting technique to carry out antibody-related tests comprises a rotator platform and a microfluidic disc set on the rotator platform, both shaped like a disc, round and flat;
    the microfluidic disc comprising a layer of microfluidic structures, wherein the layer of microfluidic structures, from the center to the periphery, comprising:
    an injection chamber with a reagent injection orifice, wherein the injection chamber is configured on the center of the microfluidic disc and the center of the layer of the microfluidic structures, and wherein the reagent injection orifice is also configured on the center of the microfluidic disc;
    at least one microfluidic channel arranged radially in the layer of the microfluidic structures and connected with the injection chamber, the at least one microfluidic channel used as the channel for liquid to flow through and for reagents flowing from the center of the layer of the microfluidic structures to the periphery;
    at least one detection chamber with a sample injection orifice, placed at the periphery of the layer of the microfluidic structures and connected with the at least one microfluidic channel for the reagents to carry out reactions; and
    at least one waste chamber, set next to and connected to the at least one detection chamber for waste storage after the reactions; wherein
    the at least one microfluidic channel comprising:
    a splitting chamber set outside and connected with the injection chamber, equally splitting the reagents from the injection chamber; and
    a herringbone shape microvalve set between and connected with the splitting chamber and the at least one detection chamber, controlling the reagents flowing from the splitting chamber to the at least one detection chamber.

2. The apparatus as claimed in claim 1, wherein the layer of the microfluidic structures further comprises at least one mixing chamber with a sample injection orifice set between and connected with the herringbone shape microvalve and the at least one detection chamber.

3. The apparatus as claimed in claim 1, wherein the layer of the microfluidic structures further comprises at least one secondary microvalve set between and connected with the at least one detection chamber and the at least one waste chamber, controlling the reagents flowing from the at least one detection chamber to the at least one waste chamber.

4. The apparatus as claimed in claim 1, wherein at least one notch set evenly on the periphery of the rotator platform, the microfluidic disc fixed on the rotator platform via the at least one notch.

5. The apparatus as claimed in claim 1, wherein material of the rotator platform is aluminum.

6. The apparatus as claimed in claim 1, wherein material of the microfluidic disc is polymethylmethacrylate (PMMA).

7. The apparatus as claimed in claim 1, wherein volume of the splitting chamber is at least three times as much as the at least one detection chamber.

8. The apparatus as claimed in claim 1, wherein distance from each herringbone shape microvalve of each at least one microfluidic channel to the center of the layer of the microfluidic structures is the same.

9. An apparatus using flow splitting technique to carry out antibody-related tests comprises a rotator platform and a microfluidic disc set on the rotator platform, both shaped like a disc, round and flat;
    the microfluidic disc comprising at least two layers of microfluidic structures, wherein each layer of the at least two layers of microfluidic structures, from the center to the periphery, comprising:
    an injection chamber with a reagent injection orifice, wherein the injection chamber is configured on the center of the microfluidic disc and the center of the at least two layers of the microfluidic structures, and wherein the reagent injection orifice is also configured on the center of the microfluidic disc;
    at least one microfluidic channel arranged radially in the at least two layers of the microfluidic structures and connected with the injection chamber, the at least one microfluidic channel used as the channel for liquid to flow through and for reagents flowing from the center of the at least two layers of microfluidic structures to the periphery;
    at least one detection chamber with a sample injection orifice placed at the periphery of the at least two layers of the microfluidic structures for the reagents to carry out reactions and connected with each at least one microfluidic channel placed in the different layers but at the same position corresponding to that in an upper layer and a lower layer of the at least two layers of the microfluidic structures; and at least one waste chamber set next to and connected to the at least one detection chamber for waste storage after the reactions; wherein the at least one microfluidic channel comprising:

a splitting chamber set outside and connected with the injection chamber, equally splitting the reagents from the injection chamber; and a herringbone shape microvalve set between and connected with the splitting chamber and the at least one detection chamber, controlling the reagents flowing from the splitting chamber to the at least one detection chamber.

10. The apparatus as claimed in claim 9, wherein the at least two layers of the microfluidic structures comprise at least one mixing chamber with a sample injection orifice set between and connected with the herringbone shape microvalve and the at least one detection chamber.

11. The apparatus as claimed in claim 9, wherein the at least two layers of the microfluidic structures comprises at least one secondary microvalve set between and connected with the at least one detection chamber and the at least one waste chamber, controlling the reagents flowing from the at least one detection chamber to the at least one waste chamber.

12. The apparatus as claimed in claim 9, wherein at least one notch set evenly on the periphery of the rotator platform, the microfluidic disc fixed on the rotator platform via the at least one notch.

13. The apparatus as claimed in claim 9, wherein material of the rotator platform is aluminum.

14. The apparatus as s claimed in claim 9, wherein material of the microfluidic disc is polymethylmethacrylate (PMMA).

15. The apparatus as claimed in claim 9, wherein each injection chamber with the reagent injection orifice in different layers of the at least two layers of microfluidic structures is not mutually connected.

16. The apparatus as claimed in claim 9, wherein volume of the splitting chamber is at least three times as much as the at least one detection chamber.

17. The apparatus as claimed in claim 9, wherein distance between each herringbone shape microvalve in the same layer of the at least two layers of microfluidic structures and the center of the at least two layers of microfluidic structures is the same.

* * * * *